(12) United States Patent
Raistrick et al.

(10) Patent No.: US 7,377,924 B2
(45) Date of Patent: May 27, 2008

(54) NAVIGATED DRILL GUIDED RESECTION BLOCK

(75) Inventors: James W. Raistrick, Hoboken, NJ (US); Knute C. Buehler, Bend, OR (US); Carlos E. Collazo, Old Greenwich, CT (US)

(73) Assignee: Howmedica Osteonics Corp., Mahwah, NJ (US)

( * ) Notice: Subject to any disclaimer, the term of this patent is extended or adjusted under 35 U.S.C. 154(b) by 35 days.

(21) Appl. No.: 10/937,587

(22) Filed: Sep. 9, 2004

(65) Prior Publication Data

US 2006/0064105 A1    Mar. 23, 2006

(51) Int. Cl.
A61F 5/00 (2006.01)
(52) U.S. Cl. ....................................................... 606/87
(58) Field of Classification Search ............ 606/86–89, 606/96
See application file for complete search history.

(56) References Cited

U.S. PATENT DOCUMENTS

| | | | |
|---|---|---|---|
| 3,457,922 A | 7/1969 | Ray |
| 4,703,751 A | 11/1987 | Pohl |
| 4,809,694 A | 3/1989 | Ferrara |
| 4,952,213 A | 8/1990 | Bowman et al. |
| 5,263,956 A | 11/1993 | Nobles |
| 5,279,575 A | 1/1994 | Sugarbaker |
| 5,342,368 A | 8/1994 | Petersen |
| 5,364,401 A | 11/1994 | Ferrante et al. |
| 5,375,586 A | 12/1994 | Yoon |
| 5,443,464 A | 8/1995 | Russell et al. |
| 5,514,139 A | 5/1996 | Goldstein et al. |
| 5,597,379 A | 1/1997 | Haines et al. |
| 5,643,272 A | 7/1997 | Haines et al. |
| 5,658,272 A | 8/1997 | Hasson |
| 5,681,316 A | 10/1997 | DeOrio et al. |
| 5,690,632 A | 11/1997 | Schwartz et al. |
| 5,755,803 A | 5/1998 | Haines et al. |
| 5,810,712 A | 9/1998 | Dunn |
| 5,810,827 A | 9/1998 | Haines et al. |

(Continued)

FOREIGN PATENT DOCUMENTS

DE    202 02 615 U1    6/2002

(Continued)

OTHER PUBLICATIONS

EP Search Report, Jul. 20, 2007.

Primary Examiner—Eduardo C. Robert
Assistant Examiner—Michael J. Araj
(74) Attorney, Agent, or Firm—Lerner, David, Littenberg, Krumholz & Mentlik, LLP

(57) ABSTRACT

A bone cutting guide block has a cutting tool guide surface and a navigation mount for a navigation tracker component for computer aided positioning of the guide for a resection procedure. In various embodiments, the guide includes a rotation means. Preferably, a swivel with a pivot apparatus is provided to limit rotation to permit controlled flexion-extension angle about the pivot with respect to the cutting guide surface. A fixing member through the swivel permits for varus-valgus adjustment of the guide surface. Optionally, a positioning actuator and/or biased resistance actuator implements more regulated flexion-extension angle adjustment with the swivel. Various traversing mechanisms, such as a threaded wheel or pivoted cam tool permit controlled proximal-distal adjustment of the cutting guide surface.

36 Claims, 14 Drawing Sheets

U.S. PATENT DOCUMENTS

| | | | |
|---|---|---|---|
| 5,879,354 A | 3/1999 | Haines et al. | |
| 6,056,754 A | 5/2000 | Haines et al. | |
| 6,059,788 A * | 5/2000 | Katz | 606/88 |
| 6,110,182 A | 8/2000 | Mowlai-Ashtiani | |
| 6,190,395 B1 | 2/2001 | Williams | |
| 6,195,577 B1 | 2/2001 | Truwit et al. | |
| 6,197,064 B1 | 3/2001 | Haines et al. | |
| 6,206,890 B1 | 3/2001 | Truwit | |
| 6,258,095 B1 | 7/2001 | Lombardo et al. | |
| 6,267,769 B1 | 7/2001 | Truwit | |
| 6,267,770 B1 | 7/2001 | Truwit | |
| 6,306,146 B1 | 10/2001 | Dinkler | |
| 6,385,475 B1 | 5/2002 | Cinquin et al. | |
| 6,514,259 B2 * | 2/2003 | Picard et al. | 606/88 |
| 6,579,281 B2 | 6/2003 | Palmer et al. | |
| 6,695,848 B2 | 2/2004 | Haines | |
| 6,712,824 B2 * | 3/2004 | Millard et al. | 606/87 |
| 6,796,986 B2 * | 9/2004 | Duffner | 606/87 |
| 7,029,477 B2 | 4/2006 | Grimm | |
| 2001/0018589 A1 * | 8/2001 | Muller | 606/88 |
| 2002/0107522 A1 | 8/2002 | Picard et al. | |
| 2002/0133160 A1 | 9/2002 | Axelson et al. | |
| 2002/0133163 A1 | 9/2002 | Moctezuma et al. | |
| 2003/0040753 A1 | 2/2003 | Daum et al. | |
| 2003/0055436 A1 | 3/2003 | Daum et al. | |
| 2003/0069591 A1 | 4/2003 | Carson et al. | |
| 2003/0171757 A1 | 9/2003 | Coon et al. | |
| 2004/0039396 A1 | 2/2004 | Couture et al. | |
| 2004/0122436 A1 | 6/2004 | Grimm | |
| 2005/0209605 A1 * | 9/2005 | Grimm et al. | 606/96 |

FOREIGN PATENT DOCUMENTS

| | | |
|---|---|---|
| DE | 10258322 B3 | 4/2004 |
| EP | 0 469 966 A1 | 2/1992 |
| EP | 0 490 812 A1 | 6/1992 |
| EP | 1 442 712 A | 8/2004 |
| WO | WO-92/03993 | 3/1992 |
| WO | WO-94/00066 A1 | 1/1994 |
| WO | WO-98/20799 | 5/1998 |
| WO | WO-2004/017843 A | 3/2004 |

* cited by examiner

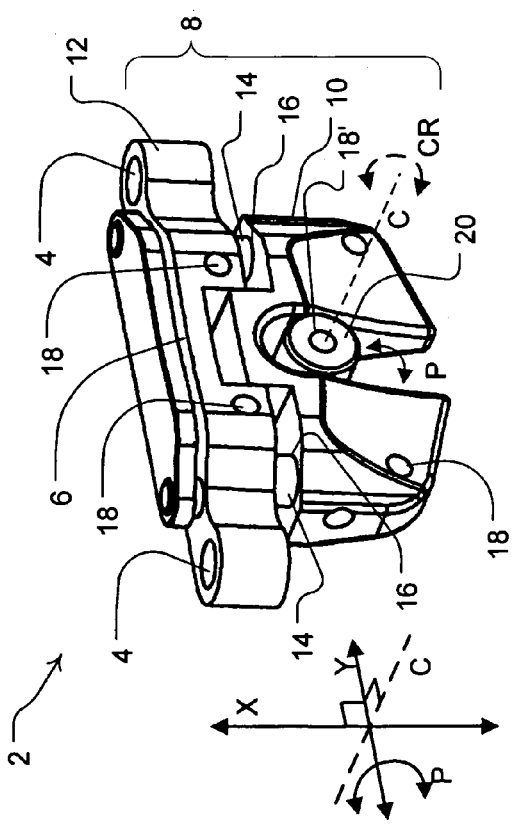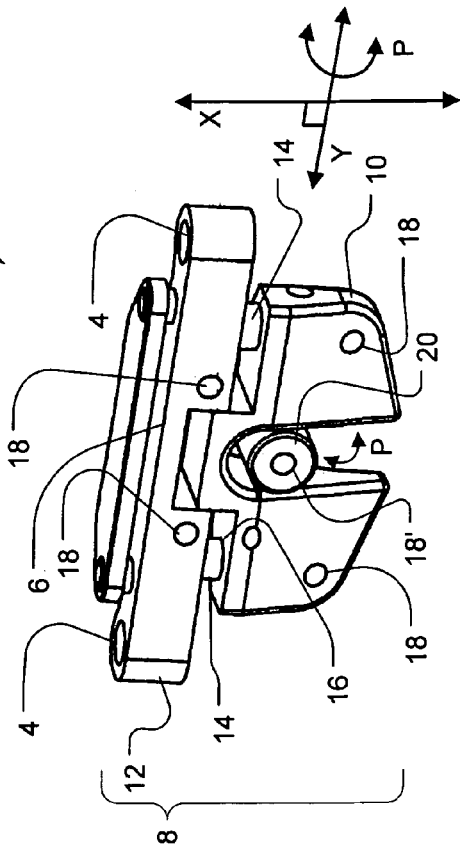
FIG. 1
FIG. 2

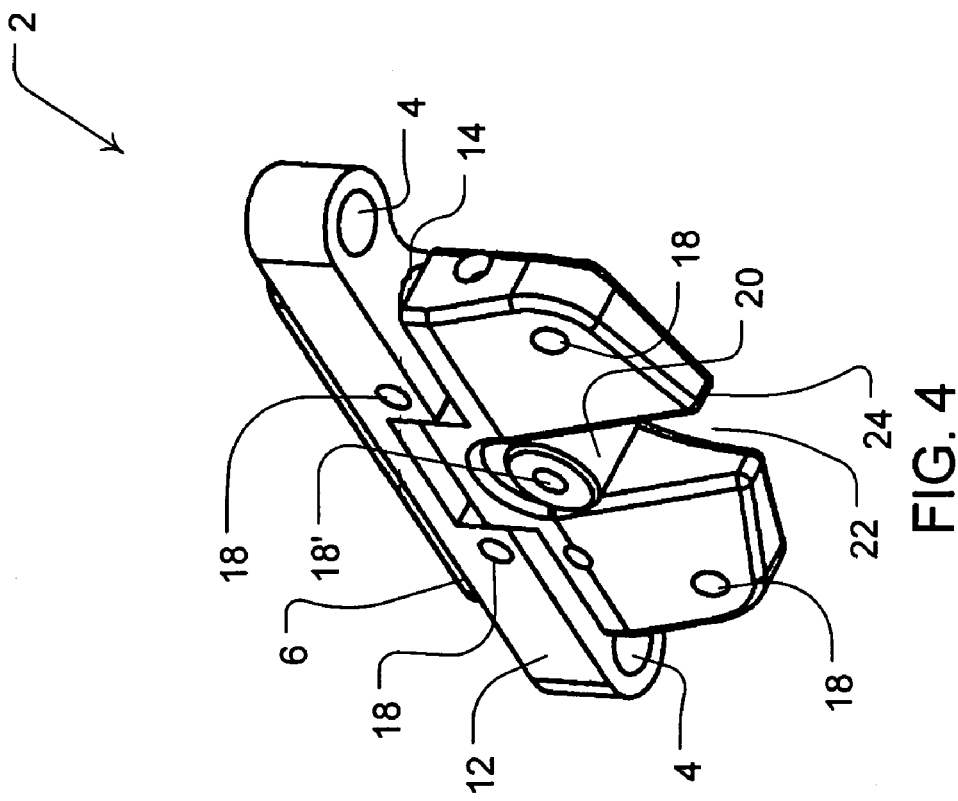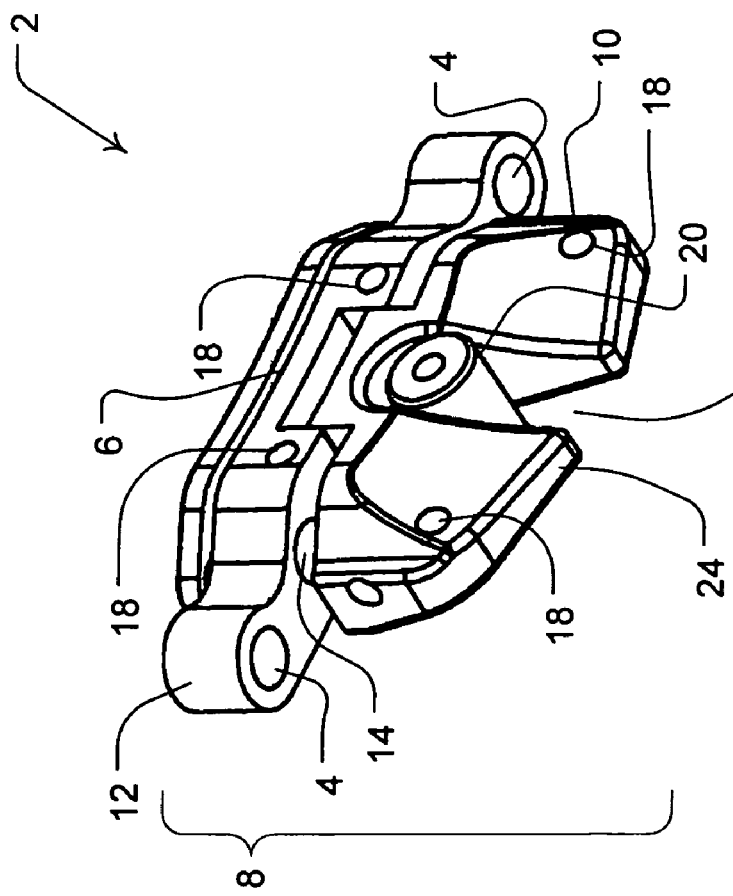

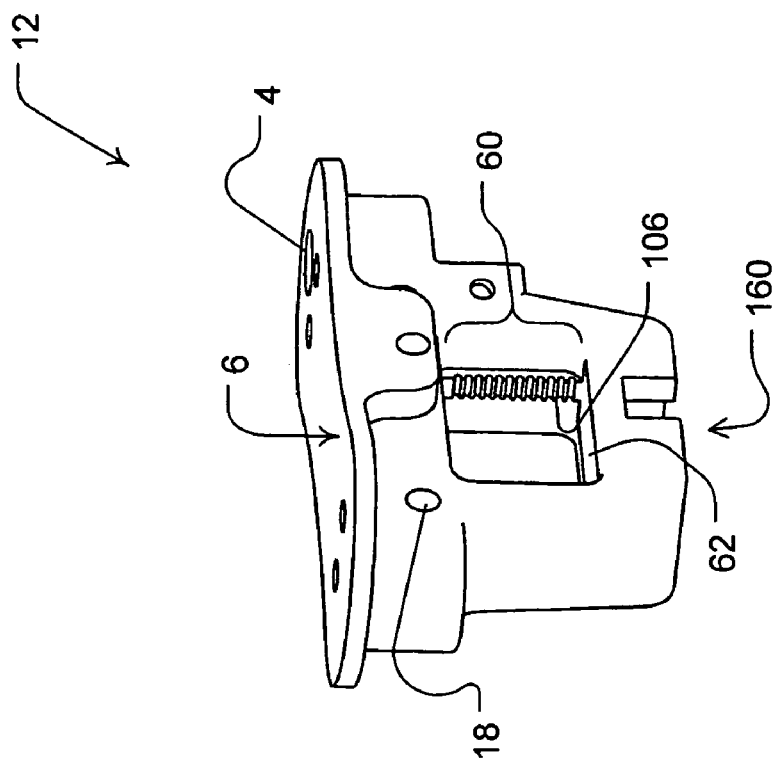
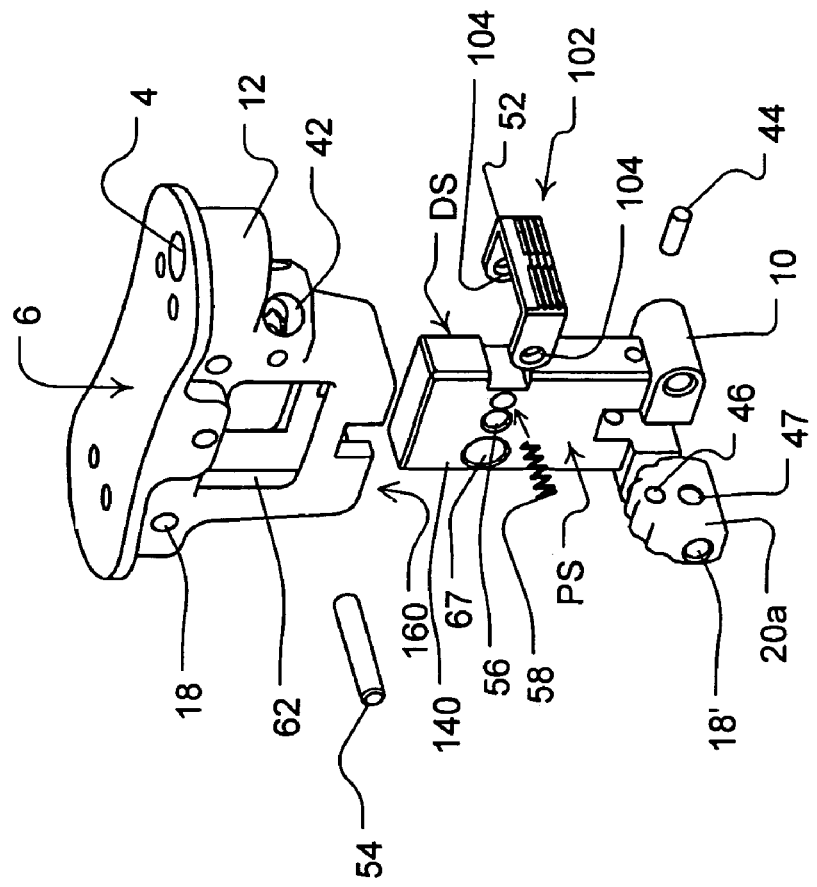

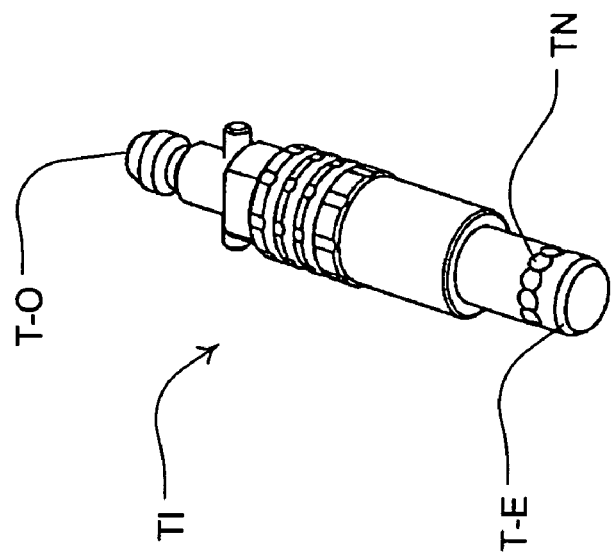
FIG. 21
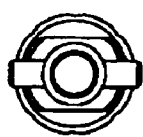
FIG. 20
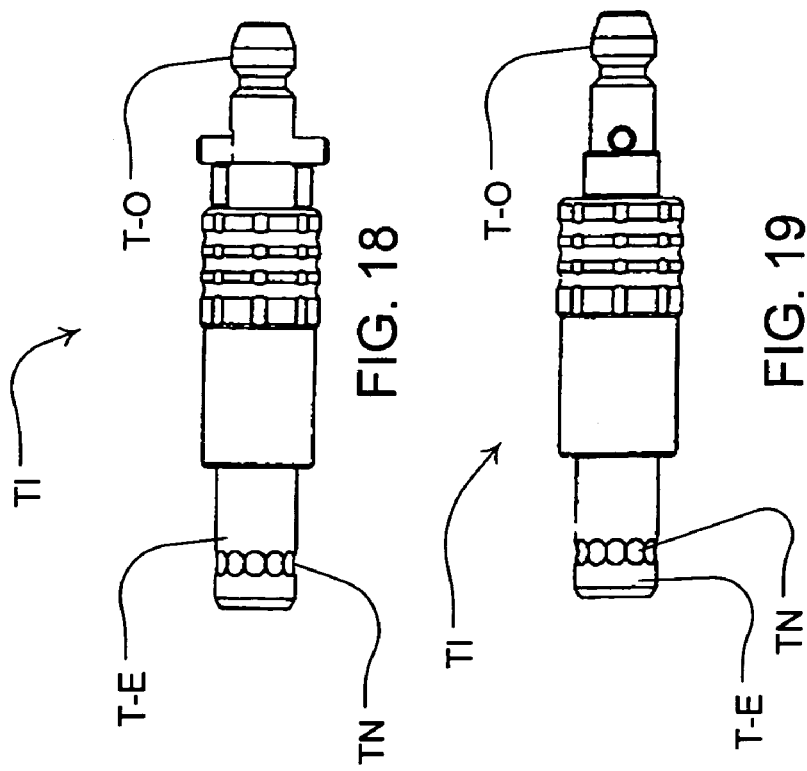
FIG. 18
FIG. 19

NAVIGATED DRILL GUIDED RESECTION BLOCK

FIELD OF THE INVENTION

The present invention relates to surgical devices. More particularly, the invention involves a cutting block configured for navigated positioning with an automated tracker system and adjustment devices for precision alignment of the cutting block in response to information from the tracker system.

BACKGROUND OF THE INVENTION

Total knee arthroplasty involves replacement of portions of the patella, femur and tibia with artificial components. In particular, a proximal portion of the tibia and a distal portion of the femur are cut away (resected) and replaced with artificial components. In performing this knee surgery, it has been desirable to minimize the size of the incision to thereby minimize damage to soft tissue.

In particular, it is necessary to resect the proximal tibia and distal femur with, among other cuts, a facing pair of planer cuts from which other bone cuts, in the case of the femur, can be referenced.

In order to make these cuts, resecting the femur and tibia necessitates significant cutting of soft tissue, including muscles, tendons and ligaments.

As used herein, when referring to bones or other parts of the body, the term "proximal" means closer to the heart and the term "distal" means more distant from the heart. When referring to instruments, the term "proximal" means closer to the physician or user and the term "distal" means more distant from the physician or user.

There are several types of knee prosthesis known in the art. One type is sometimes referred to as a "resurfacing type." In these prostheses, the articular surface of the distal femur and the proximal tibia are "resurfaced" with respective metal and plastic condylar-type articular bearing components.

One important aspect of these procedures is the correct resection of the distal femur and proximal tibia. These resections must provide planes which are correctly angled in order to properly accept and align the prosthetic components. In particular, the resection planes on the tibia and femur must be correctly located relative to at least three parameters: proximal-distal location; varus-valgus angle; and flexion-extension angle.

Moreover, following distal resection, the femur must be further shaped with the aid of a cutting block, the cutting block must be correctly located relative to internal-external rotation, medial-lateral position and anterior-posterior position.

Various computerized systems have been introduced to aid the practitioner during the surgical procedure by improving accuracy of the cuts. In one such system, the mechanical axis of the tibia and femur is identified with the system which then provides the ability to align the cutting block to the mechanical axis and after resection to verify the bone cuts. In these systems, multiple cameras are deployed above the surgical site to observe a plurality of dynamic reference frame devices also known as trackers. These trackers are attached to body parts and the surgical instruments and preferably include light emitting devices, such as light emitting diodes, which are visible to the cameras. Using software designed for a particular surgical procedure, a computer receiving input from the camera guides the placements of the surgical instruments with respect to the patient's mechanical axis. Such systems are shown in U.S. Pat. No. 6,385,475, the teachings of which are incorporated herein by reference.

Generally, the cutting block coupled to a tracker will be manually or free-handedly moved by the surgeon with the assistance of feedback from the computer system while the computer monitors movement of the tracker so that the block can be positioned in the desired position with regard to the patient's mechanical axis. However, finely adjusting the position of such devices even with the assistance of the computer system may still require substantial skill of the surgeon due to the manual or free hand nature of the movement or re-positioning of the block and tracker.

Improvements to such block and tracker devices can be desirable to maximize the potential of the positioning information of the computer system and to minimize the skill necessary to align the block and tracker in a minimally invasive soft tissue friendly incision so that the cutting guide will be located in the most advantageous position for a resection necessary during such an operation.

SUMMARY OF THE INVENTION

The invention includes a surgical cutting block apparatus for performing a minimally invasive resection procedure with a cutting instrument. The guide is preferably used to make either the proximal tibial surface resection or the distal femoral surface resection. The cutting block preferably is a component of navigation tracker system for computer aided orientation. The cutting block preferably includes a guide extension having a tracker mount for use with a tracker device that provides information for the navigation system for guiding orientation of the cutting block. The guide extension also includes a cutting guide for guiding a cutting instrument for a resection procedure. A main body coupled with the guide extension is mountable with a receiving surface, such as a bone for a resection. A swivel coupled with the main body by a pivot is configured to receive a fixing member through the swivel. The fixing member limits movement of the main body with respect to the receiving surface when fixed through the swivel to the receiving surface. The fixing member has a central axis along its length. The pivot is configured to limit relative rotation between the swivel and the main body about a single axis where the single axis is generally perpendicular to the first axis.

In another embodiment, the cutting block apparatus for performing a minimally invasive bone resection procedure with a navigation tracker system includes a guide unit fixable to a bone surface for a resection. The guide unit has a cutting guide surface for guiding a bone cutting tool for resecting the bone. The guide unit also has a tracker mount for mounting a component of a navigation tracker system with the guide unit. A swivel in this embodiment is coupled to the guide unit. The swivel is fixable with the bone surface with a fixing member. Preferably, the swivel has a range of rotation relative to the main body to change the orientation of the cutting guide surface when the swivel is fixed to the bone surface with the fixing member. The swivel is also configured with a tactile mechanism for tactilely indicating selective positioning of the swivel in the range of motion.

In another embodiment, the computer navigable cutting guide apparatus for a minimally invasive bone resection procedure has an adjustable guide means for guiding a cutting tool for the bone resection procedure. The adjustable guide means is fixable to a bone to be resected. A navigation tracker mounting means is connected to the adjustable guide means for receiving a component of a navigation system for navigation of a cutting guide surface of the adjustable guide means. A rotation means is rotatably joined with the adjustable guide means for flexion-extension angle adjustment of the cutting guide surface. This rotation means is rotatably fixable to the bone for varus-valgus angle adjustment of the cutting guide surface. Moreover, the apparatus preferably includes a tactile positioning actuator for tactile positioning adjustment of the flexion-extension angle with the rotation means.

A unique method for forming a planar surface on a bone involving several steps is permitted by providing such a two part cutting block operable for interfacing with a computer-aided navigation system. With the computer-aided navigation system, a first part of the two part cutting block with a planar cutting guide surface is approximately located in a proximal-distal direction on the bone near the necessary cutting position. Again using the computer-aided navigation system the rotational position of a second part of the cutting block is set about first and second axes generally perpendicular to the proximal-distal direction. After such positioning in this way, the second part of the block is pinned to the bone with a first pin. After such pinning to the bone, the user verifies and, if necessary, readjusts the rotational position of the cutting block about the first and second axes using the navigation system and then pins the second part of the block to the bone. This second pinning prevents rotation of the block about the first and second axes. Then, the practitioner verifies and, if necessary, readjusts the proximal-distal location of the first part using the navigation system by moving the first part in the proximal-distal direction with respect to the pinned second part. The planar bone surface may then be formed with the cutting guide on the first part of the cutting block.

Additional aspects of the invention will be apparent from a review of the following disclosure and claims.

BRIEF DESCRIPTION OF THE DRAWINGS

FIG. 1 is a perspective view showing a distal side of an illustrative embodiment of a cutting block of the invention;

FIG. 2 is a perspective view showing a proximal side of the embodiment of the cutting block of FIG. 1;

FIG. 3 is another perspective view showing the distal side of the embodiment of a cutting block of FIG. 1;

FIG. 4 is a another perspective view showing the proximal side of the cutting block of FIG. 1;

FIG. 12 is an exploded perspective view of some of the components of the embodiment of the cutting block of FIG. 11;

FIG. 13 is a perspective view of a guide extension component of the embodiment of the cutting block of FIG. 11;

FIG. 18 is a side elevation view of an illustrative embodiment of a tracker interface mountable with a cutting block of the invention;

FIG. 19 is another side elevation view of the illustrative embodiment of a tracker interface of FIG. 18;

FIG. 20 is a tracker top elevation view of the tracker interface of FIG. 18; and FIG. 21 is a perspective view of the tracker interface of FIG. 18.

DETAILED DESCRIPTION

Figure 5:
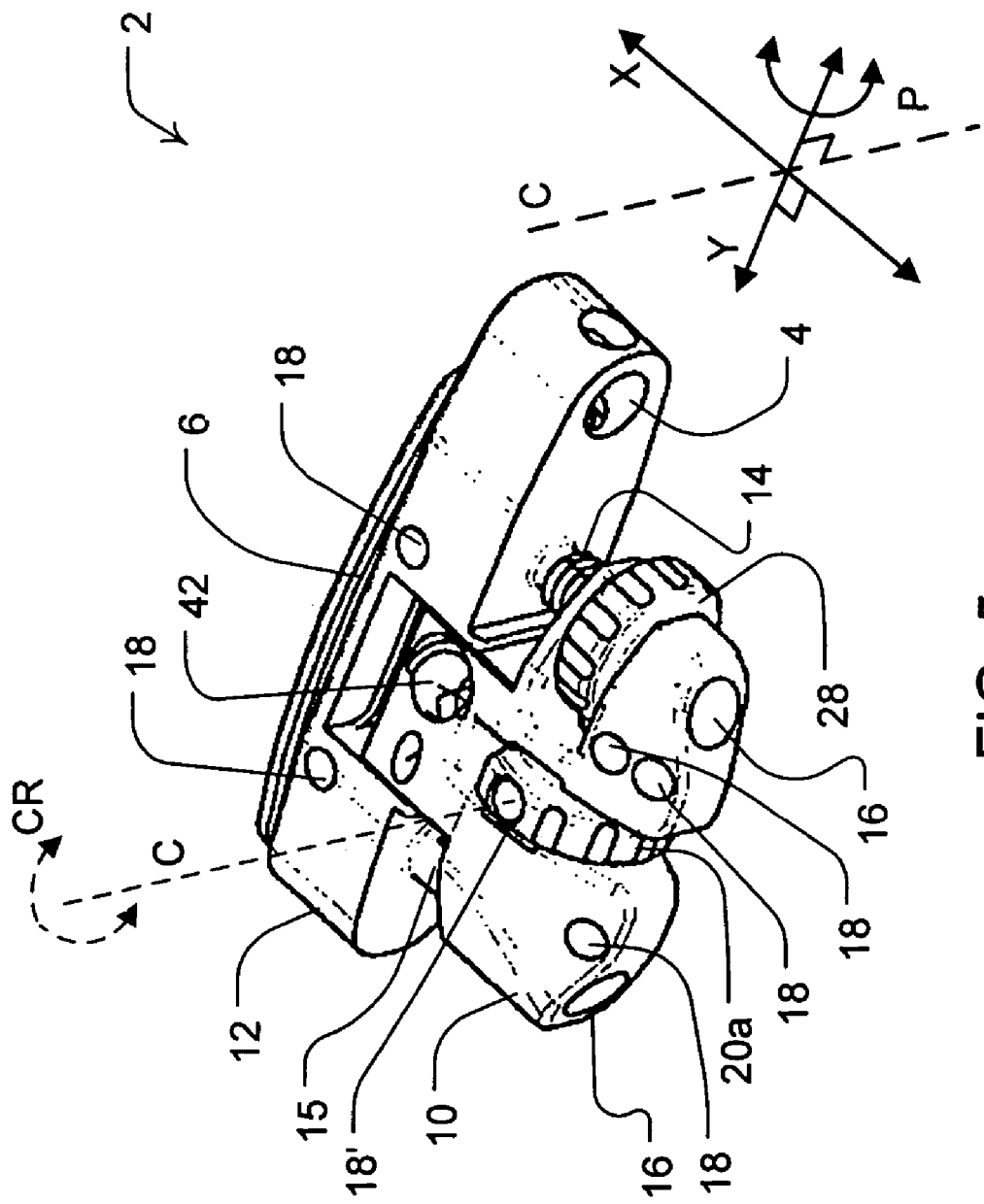
FIG. 5 is a perspective view of another illustrative embodiment of a cutting block of the invention.
Figure 6:
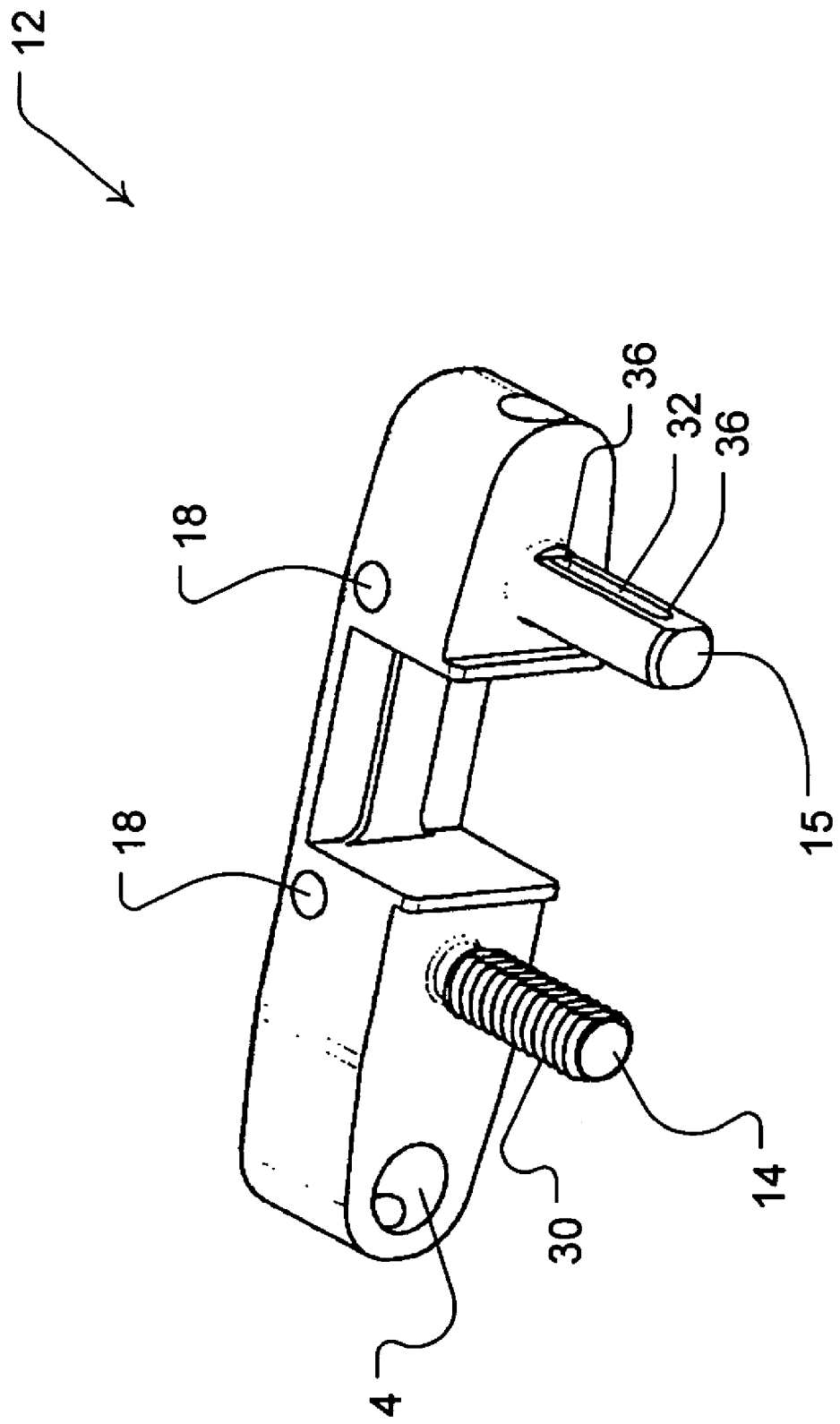
FIG. 6 is a perspective view of a guide extension component of the cutting block of FIG. 5.
Figure 7:
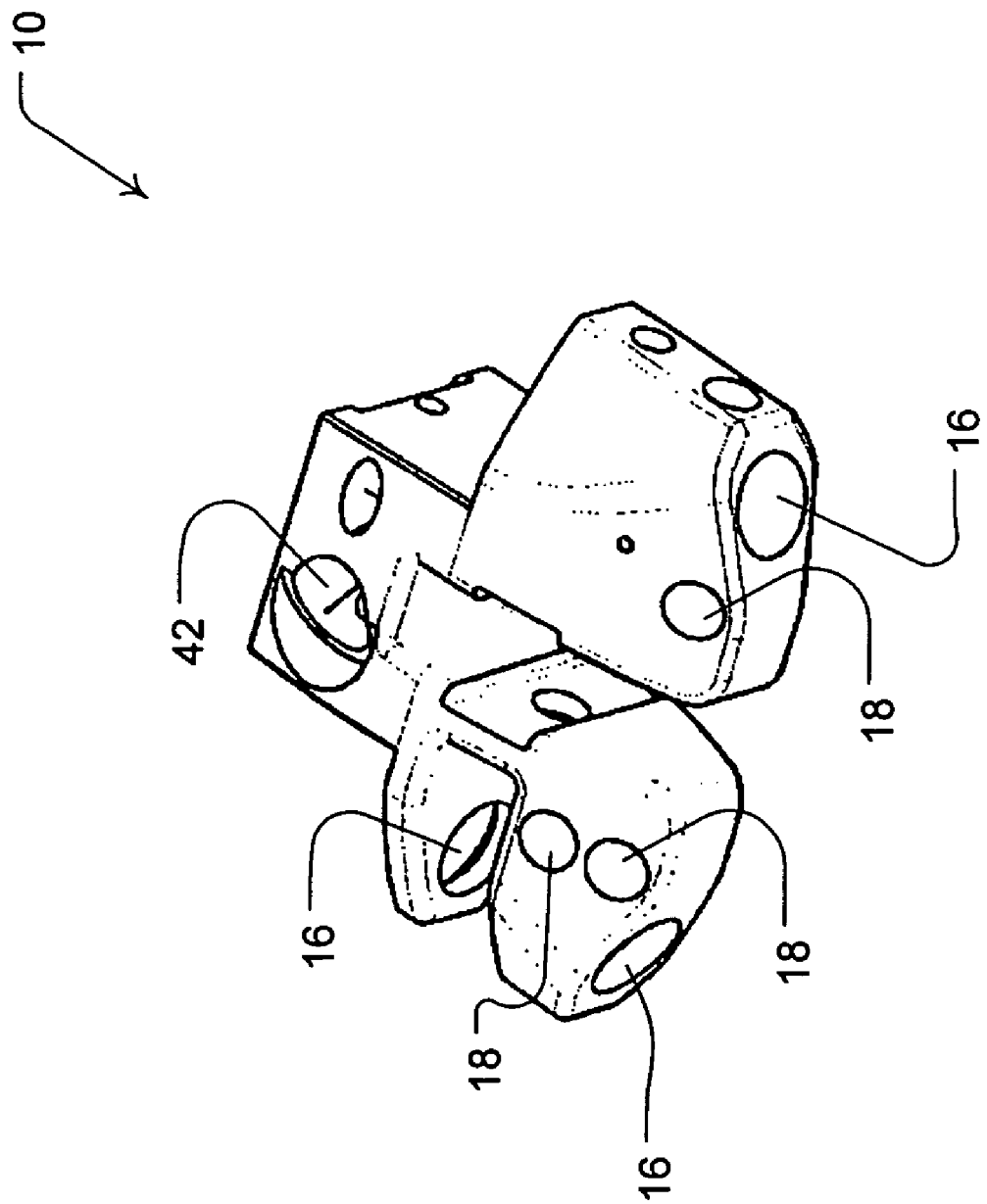
FIG. 7 is a perspective view of a main body component of the cutting block of FIG. 5.

Referring to the figures, a cutting block 2 of the invention generally includes a tracker mount 4, a cutting guide 6, and a guide body 8. One embodiment of such an apparatus is illustrated in FIGS. 1 through 4. In this embodiment, the guide body 8 includes a main body 10 and a guide extension 12. When these devices are coupled they form a unit that can serve as an adjustable cutting guide. To this end, the guide extension 12 supports the cutting guide 6 to provide a surface to guide a cutting instrument. As illustrated, the cutting surface has at least one planar surface (easily viewed in FIG. 10) on which a blade may rest during a resection procedure. In this embodiment of FIGS. 1 through 4, the cutting guide 6 is illustrated for preference as a slotted guide sized for a blade of a cutting instrument. However, other instrument guides, such as an open face guide or modular slotted guide may be utilized.

Figure 10:
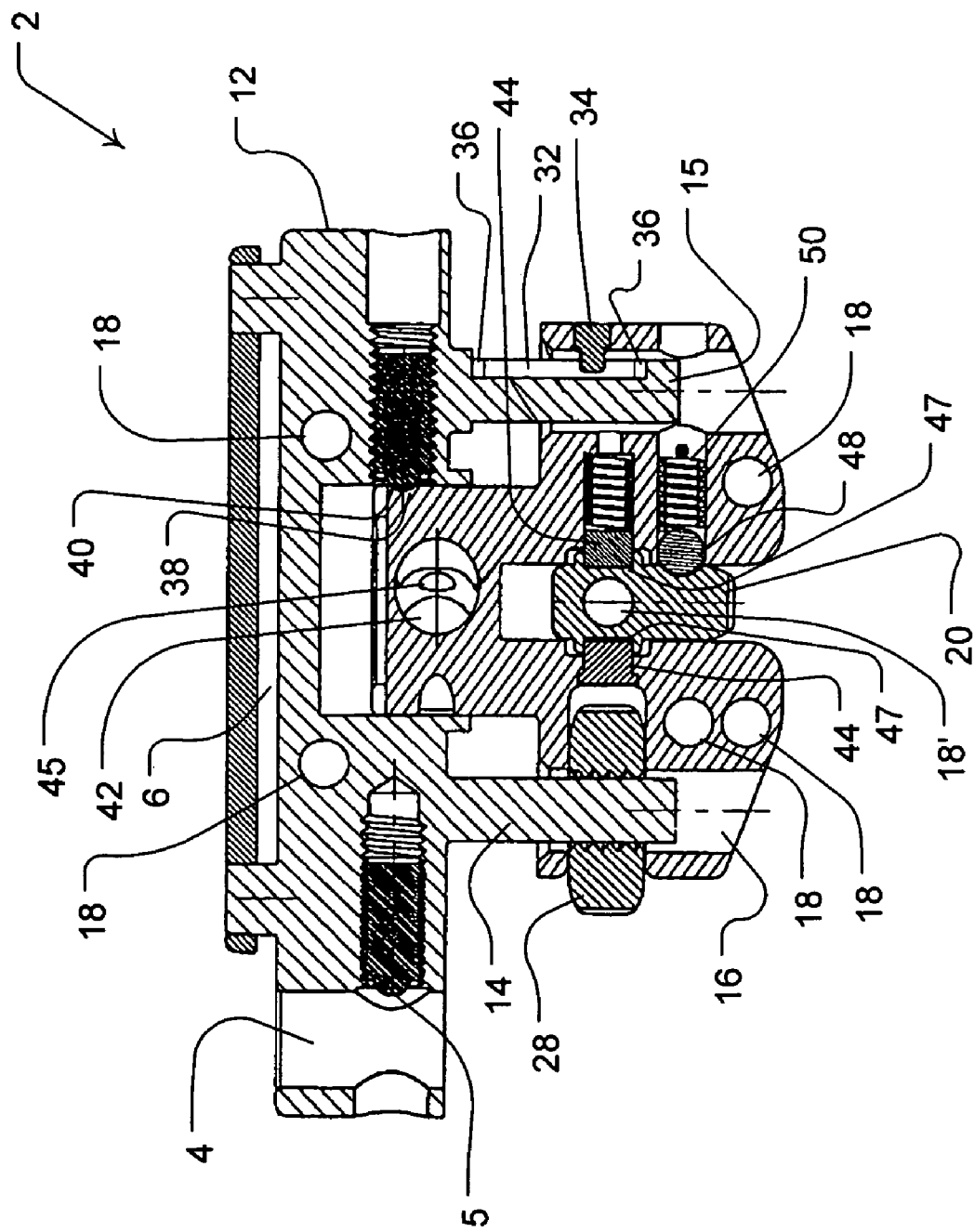
FIG. 10 is a section view of the embodiment of the cutting block of FIG. 5 taken along line A-A of FIG. 9.

The guide extension 12 further includes one or more tracker mounts 4. The tracker mount serves as a location for mounting or coupling a tracker to the cutting block 2. For example, the tracker mount 4 of the cutting block of FIGS. 1 through 4, is an aperture to receive a tracker interface TI or extension illustrated in FIG. 18 through 21. End T-E of the tracker would be removeably coupled to the tracker mount 4 aperture. The opposite end T-O of the tracker interface TI would then be coupled to a tracker T. As illustrated in FIG. 10, a ball plunger 5 that is spring loaded serves to secure the tracker interface when it is installed in the aperture of the tracker mount 4. It also provides tactile indexed orientation of the tracker interface in conjunction with tracker interface indents TN as the ball plunger 5 enters and exits the indents TN (illustrated in FIGS. 18, 19 and 21) when the tracker interface is rotated within the tracker mount 4.

In this embodiment of FIGS. 1, 2, 5 and 11, the guide extension 12 is configured with the main body 10 to permit the guide extension 12 to traverse axially away from or towards the main body 10. Such movement is illustrated with respect to the axis X illustrated in FIGS. 1 through 4. Preferably, the axis X is generally perpendicular to the planar guiding surface of the cutting guide 6 against which the cutting blade will oscillate during a resection procedure. Translation along the axis X may be utilized to permit proximal-distal location adjustment of the cutting guide 6 surface. In this example, the guide extension 12 includes traversing posts 14. These posts preferably extend into correspondingly sized post apertures 16 of the main body 10, permitting the relative movement therebetween along the axis X. As illustrated, the posts are generally perpendicular to the mentioned planar guiding surface. For preference in this embodiment proximal-distal translation along axis X is limited to about 8 mm. Further translation will separate the main body 10 from the guide. Thus, when the main body 10 and guide extension are centered along the translation axis, translation preferably may extend distally or proximally by about 4 mm.

In this embodiment, this axial translation may be implemented by hand, although other adjustment mechanisms may be utilized. Preferably, the main body 10 and the guide extension 12 include pin holes 18 extending through the cutting block 2. The pin holes are sized to receive fixing members or pins for fixing the cutting block 2 to a receiving surface by insertion of a pin through the cutting block 2 and into the surface, such as a bone (e.g., Tibia or Femur) for a bone resection procedure. In this embodiment axial translation is not prohibited between the main body 10 and the guide extension 12 until the main body 10 and the guide extension 12 are each fixed to the receiving surface with at least one pin or other fixing member fixed through the main body 10 and at least one pin or fixing member fixed through the guide extension 12.

The main body 10 also includes swivel 20 on a pivot about which the swivel 20 can rotate. The pivot (such as a pivot 44 having dual portions as illustrated and explained with reference to the embodiment of FIG. 10 herein) preferably limits the swivel 20 to rotate about a single axis of the pivot. In the embodiment of FIGS. 1 through 4, the swivel 20 is a cylinder having a swivel pin hole 18' extending through the cylinder for a fixing member. The pivot axis of the cylinder, illustrated in FIG. 1 as axis Y, about which the cylinder may rotate, is preferably perpendicular to the axis X along which the guide extension 12 translates relative to the main body 10. Thus, the swivel 20 may rotate about axis Y in direction of arrow P illustrated in FIGS. 1 and 2.

Preferably, such single axis rotation is for flexion/extension angle adjustment of the cutting guide surface. This rotation may be restricted by the swivel's proximity to the main body 10 so as to prevent complete rotation since a complete rotation may not be necessary during use. Thus, a swivel gap 22 in the main body 10 about the swivel 20 as illustrated in FIGS. 3 and 4 provides space to permit rotation. It is preferred that a range of such rotation be permitted to have at least 6 degrees of rotation. Thus, when in a centered position, flexion/extension angle may be adjusted plus or minus 3 degrees. However, the embodiment illustrated can have up to 30 degrees of rotation (i.e., plus or minus 15 degrees from center). To further permit rotation, in this embodiment the main body 10 also is provided with a tapered end 24. The tapered end 24 provides space between the main body 10 and the receiving surface when the swivel 20 is fixed to a receiving surface.

Preferably, the swivel is also rotatable about the fixing member or pin through the swivel pin hole 18' of the swivel 20 for varus/valgus angle adjustment of the cutting guide surface. While a swivel pin hole 18' and a pin fixing member may permit 360 degrees of rotation, such rotation about the pin should be at least about 6 degrees. Thus, when positioned on a receiving surface, proper positioning of the varus/valgus angle of the cutting block 2 can be affected by rotational movement about the pin within plus or minus 3 degrees. Rotation about a central axis C of the swivel pin hole 18' is illustrated by directional arrow CR in FIGS. 1 and 5. For preference, as illustrated in the figures, the structure of the swivel and pivot are such that the central axis C of the swivel pin hole 18', or a central axis along the length of a fixing pin through the swivel, generally intersects perpendicularly with pivot axis Y. As a result of the structure of the swivel 20 having both a pivot and swivel pin hole 18', the swivel 20 provides adjustment of the cutting block 2 with respect to flexion/extension angle positioning and varus/valgus angle positioning.

As can be seen from back face view of FIG. 1 and front face view of FIG. 2, this embodiment of the cutting block 2 has a design with a common configuration and common features on both front and back faces such that either face may be utilized as the proximate face during a resection procedure. For example, the swivel 20 is accessible from either face. With this universal design, either face of FIG. 1 or FIG. 2 may be the distal face that is the face that resides against a receiving surface of a bone for use during a resection procedure.

The components of a second embodiment of the cutting block 2 of FIGS. 1 through 4 are illustrated in FIGS. 5 through 10. In this embodiment, axial translation along axis x by the guide extension 12 with respect to the main body 10 as previously described can be actuated by use of a traversing mechanism 28. In the illustrated example, the traversing mechanism 28 is a wheel or adjustment knob that has a threaded bore and is threaded onto a traversing post 14 having complementary threads 30. Rotation of the wheel-type traversing mechanism 28 in one direction traverses the guide extension 12 in one direction along the illustrated x axis. Changing the direction of the rotation of this wheel reverses the direction of the axial translation of the guide extension 12. In this way, controlled or regulated extension of the cutting guide is permitted.

In this embodiment, to prevent rotation of guide extension 12 with respect to main body 10, a second non-threaded post 15 is provided which slidingly engages with main body 10. Optionally, non-treaded post 15 may include a channel 32. In conjunction with a key 34 inserted in the main body 10, the channel 32 and key 34 serve to limit axial translation between the main body 10 and the guide extension 12. When assembled, the key 34 moves with the main body 10 but within the channel 32. Channel ends 36 in the channel when in contact with the key 34 will serve to stop the axial translation. In this way, unintended separation of the main body 10 from the guide extension 12 may be prevented.

Since the translation between the guide extension 12 and the main body 10 has limits, it may be beneficial to provide a means for confirming their adjustment into a particular desired position. For example, a position that would center the two components can be useful such that when centered, axial translation along axis X with the traversing mechanism 28 may be permitted approximately equally in either direction along the axis from a center. To this end, main body 10 has an optional extension positioning actuator or centering indent 38 and guide extension 12 has a spring loaded ball plunger 40 as illustrated in FIG. 10. When the centering indent 38 in the main body 10 translates by the spring loaded ball plunger 40 in the guide extension 12, due to the force of the spring, the ball plunger will enter the indent. In this way, a tactile indication is generated to ensure that a desired position between the guide extension 12 and the main body 10 set by the indent has been established or selected.

Figure 14:
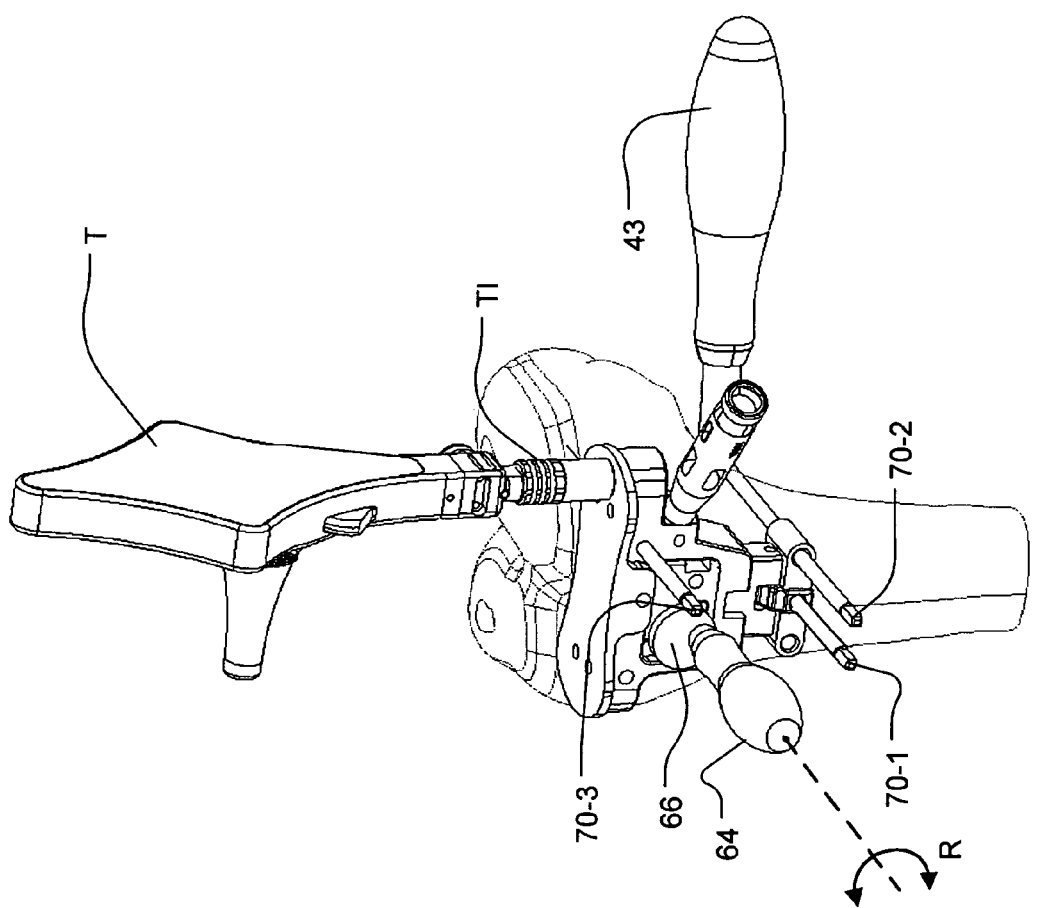
FIG. 14 is a perspective view of the embodiment of the cutting block of FIG. 11 fixed in position on a bone surface for a resection.
Figure 14B:
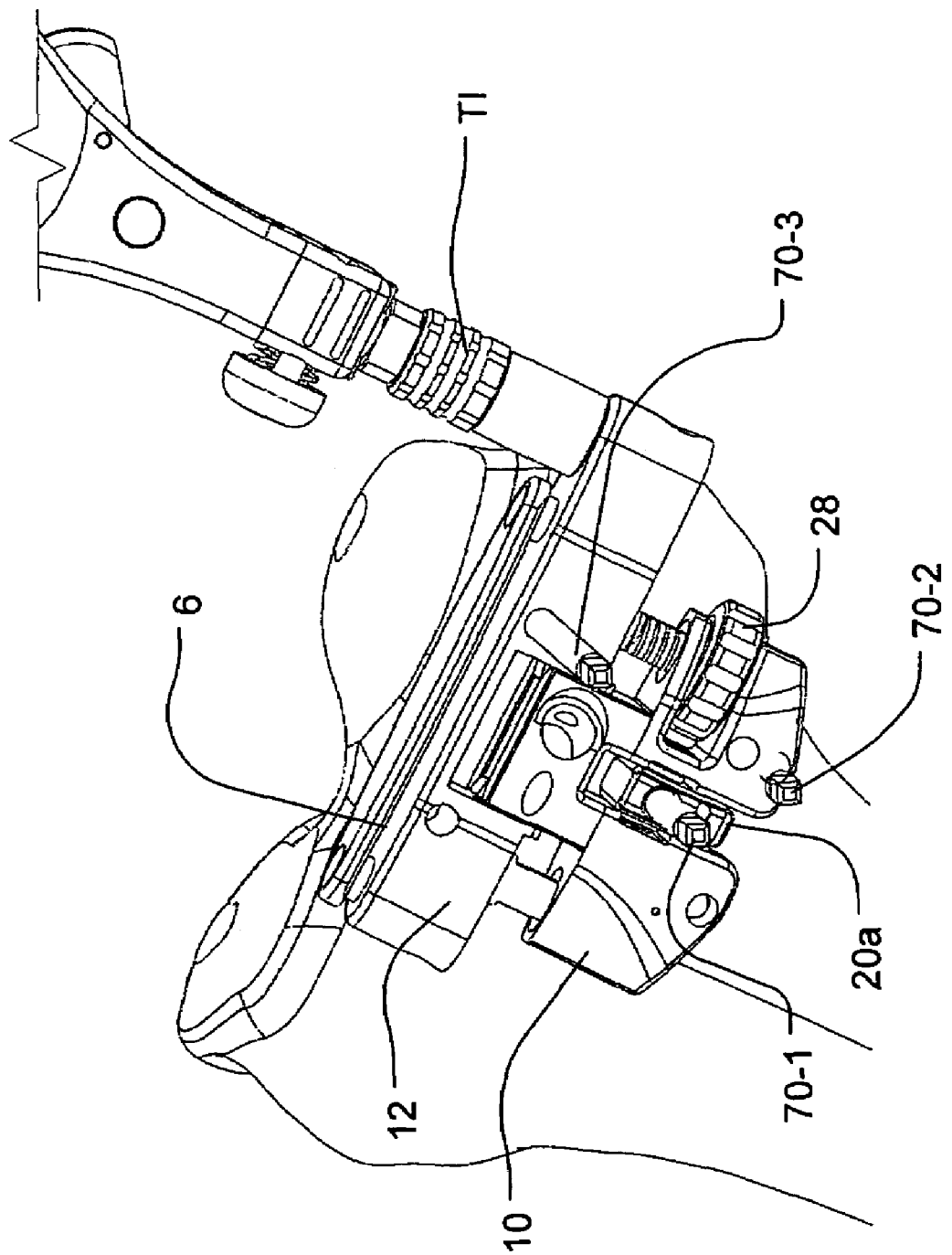
FIG. 14B is a perspective view of the embodiment of the cutting block of FIG. 5 also fixed in position on a bone surface for a resection.

In this embodiment, an optional handle mounting bore 42 is also provided. The handle mounting bore 42 is adapted to selectively couple with a modular handle 43. One such modular handle 43 is illustrated in FIG. 14. This also may be attached using a spring detent engaging a handle indent 45 in handle mounting bore 42.

In this illustrated embodiment, the swivel 20 is in the form of a swivel wheel 20a. Swivel wheel 20a, like the cylinder type swivel 20, is mounted on a pivot 44 having two portions (left and right) paired along a common axis and extending into pivot holes 47 into outer opposing sides of the swivel wheel 20a (best seen in FIG. 10). One pivot pin may be installed adjacent to a spring as shown in FIG. 10 to assist with assembly and operation.

Figure 9:
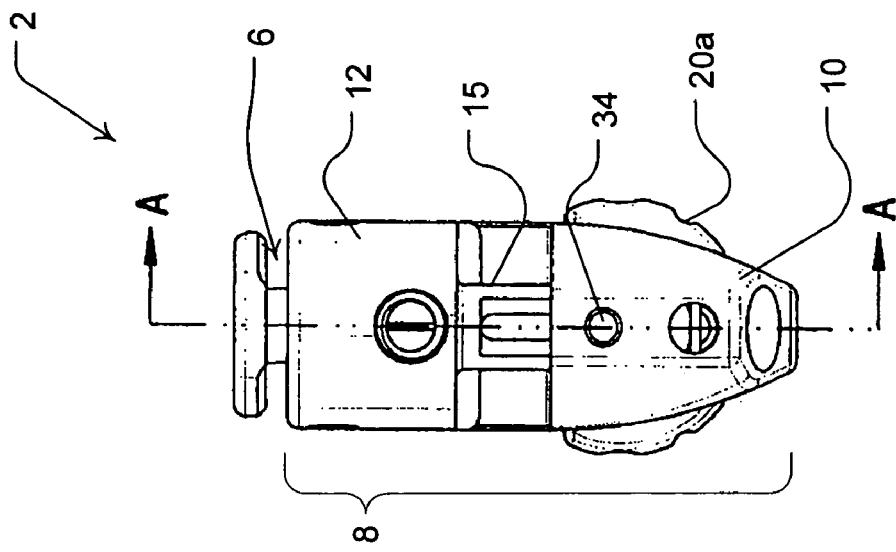
FIG. 9 is a side elevation view of the opposite side of the cutting block of FIG. 8.
Figure 9A:
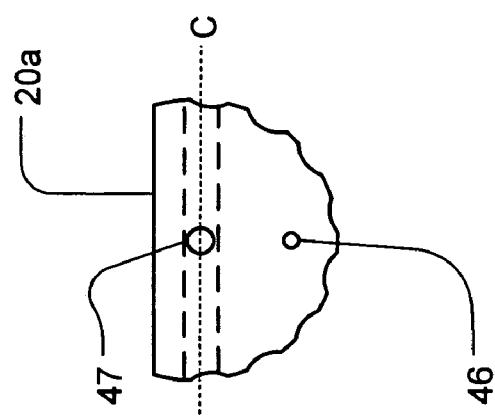
FIG. 9A is a side elevation view of a swivel wheel component of the cutting block of FIG. 5.
Figure 8:
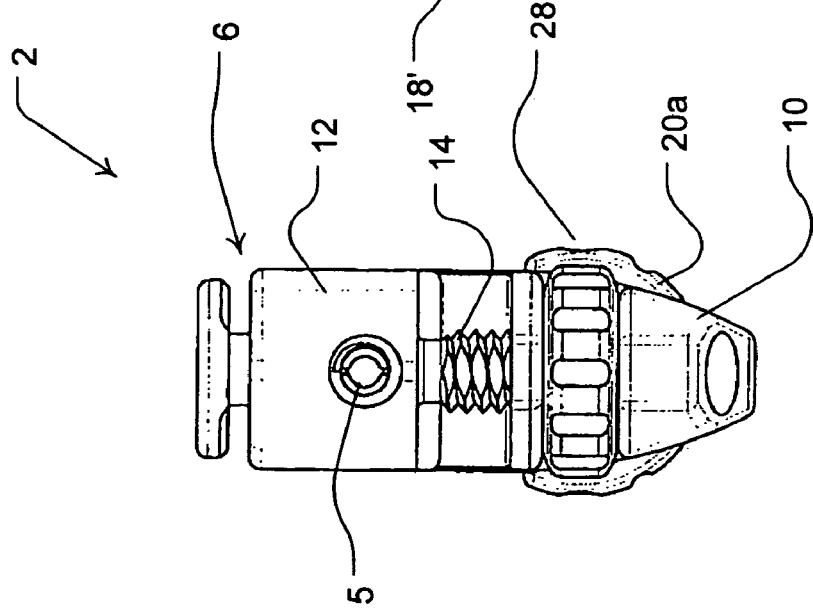
FIG. 8 is a side elevation view of the embodiment of the cutting block of FIG. 5.

For a more regulated or controlled adjustment, the swivel wheel 20a may also include positioning apparatus. For example, a wheel indent 46 is sized to fit a portion of a surface of a wheel ball 48 fitted adjacent to a wheel compression spring 50 at a side of swivel wheel 20a. As the swivel wheel is rotated, the wheel ball 48 may exit and enter indent 46 as a result of an elastic force of the wheel compression spring 50. For example, as illustrated in FIG. 9A, an indent may be provided as a centering indent to provide a tactile indication of a particular position. As shown in FIG. 9A, this wheel indent 46 provides an indicator to align a central axis C running along the center of swivel pin hole 18' through the wheel such that axis C is parallel to the surface of the cutting guide.

Optionally, additional actuators or indents may be spaced along the swivel wheel in desired or measure increments in the path of the wheel ball 48 as the swivel wheel rotates to assist with providing metered incremental adjustment with the swivel wheel. In this way, these components can serve to provide incremental adjustment with a tactile response when rotating the swivel wheel between positions set by the separate wheel indents on the swivel wheel.

Beneficially, the biased tension created by the elastic force of the wheel compression spring 50 and wheel ball 48 against the swivel wheel 20a provides a biased resistance actuator to allow for greater controlled adjustment of the swivel wheel about its pivot-related single axis of rotation (arrow P). Preferably, the resistance provided by the resistance actuator is sufficient to impede movement of the swivel wheel with respect to the guide body 8 under the weight of the guide body 8. Thus, when positioning guide body 8 adjustment of the swivel by the user/practitioner will be held constant absent additional adjusting force of the user/practitioner to facilitate fixing of the device in the adjusted position with minimal likelihood of undesired movement between swivel wheel 20a and guide body 8 about the single axis (arrow P). In this way, further regulated adjustment with the swivel wheel is permitted for purposes of adjusting the flexion/extension angle of the cutting block with or without wheel indents 46. The swivel 20 may be intentionally moved when desired with respect to guide body 8 but the spring biased resistance actuator will provide movement resistance, when movement is not desired, without the need for some release and lock mechanism before the main body 10 is fixed to the receiving surface by fixing members or pins.

As with the first embodiment, this embodiment of the cutting block also has a universal design permitting either front or back faces to serve as either bone facing surface during a resection procedure. For example, the cutting guide 6, the swivel 20, pin holes 18, swivel pin hole 18', handle mounting bore 42 and traversing mechanism 28 are all accessible for use from either face.

Figure 11:
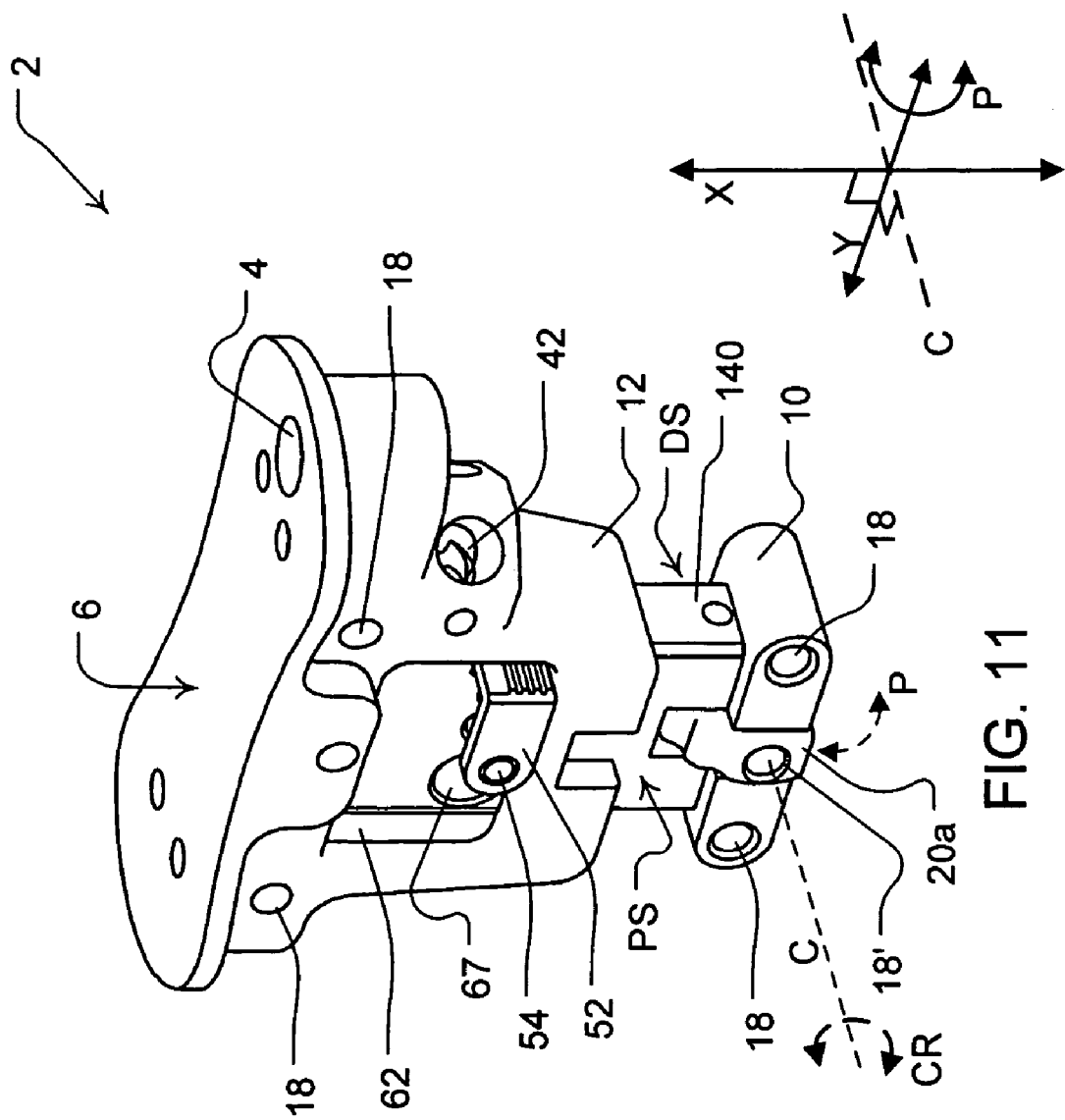
FIG. 11 is a perspective view of another illustrative embodiment of a cutting block of the invention.

A third embodiment of the cutting block 2 is illustrated in FIGS. 11 through 14 and 15. In this embodiment, the swivel 20 may be the pin cylinder of the first embodiment previously described. Alternatively, as illustrated in FIGS. 11, 12 and 14, the swivel 20 is a swivel wheel 20a, which may optionally be implemented for tactile/regulated adjustment by one or more positioning actuators and/or a resistance actuator as previously described with respect to the second embodiment. Therefore, adjustment of the cutting block 2 of this embodiment for purposes of flexion/extension and varus/valgus using the swivel 20 is like that of the previously described embodiments.

Figure 15:
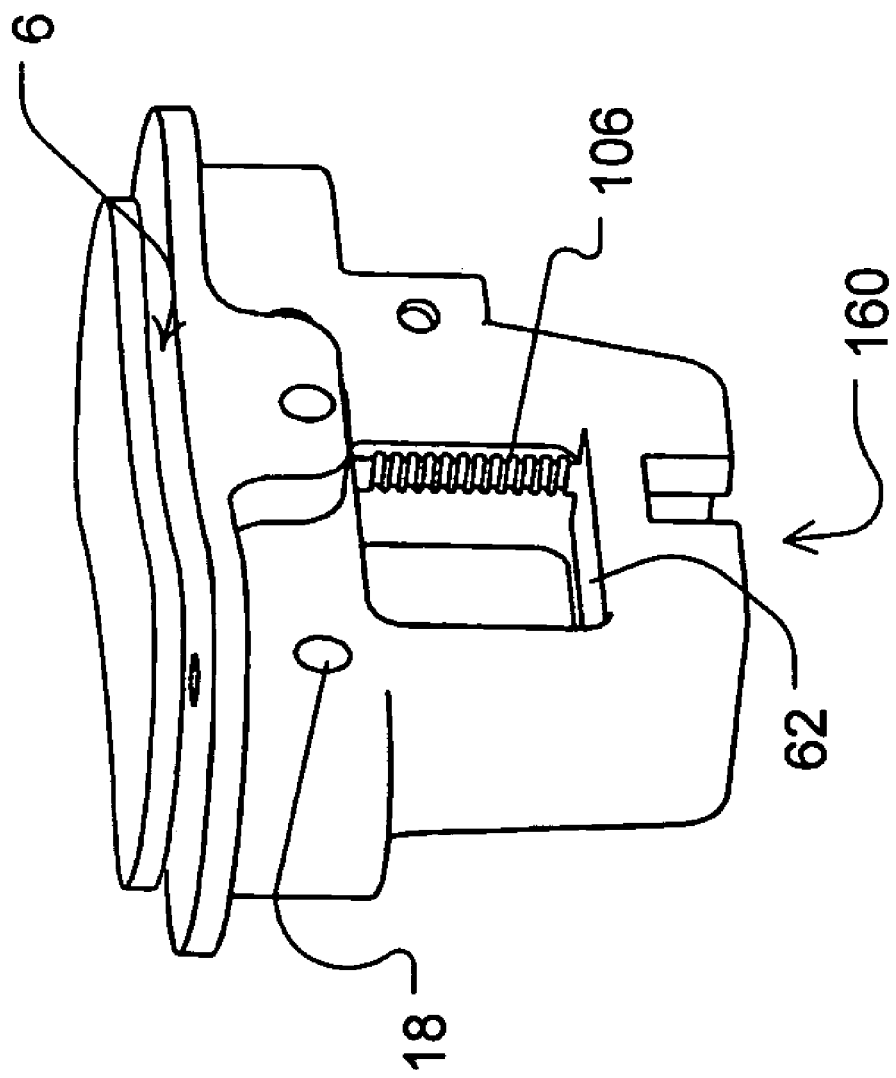
FIG. 15 is a perspective view of a guide extension component of the embodiment of the cutting guide of FIG. 11 with a removable slotted guide component (e.g., a modular capture) added to the open surface guide extension component.
Figure 16:
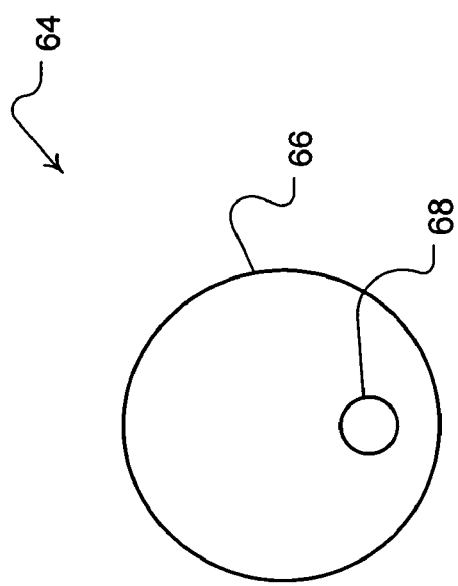
FIG. 16 bottom view of the cam portion of the extension tool for adjusting the embodiment of the cutting block illustrated in FIG. 11.
Figure 17:
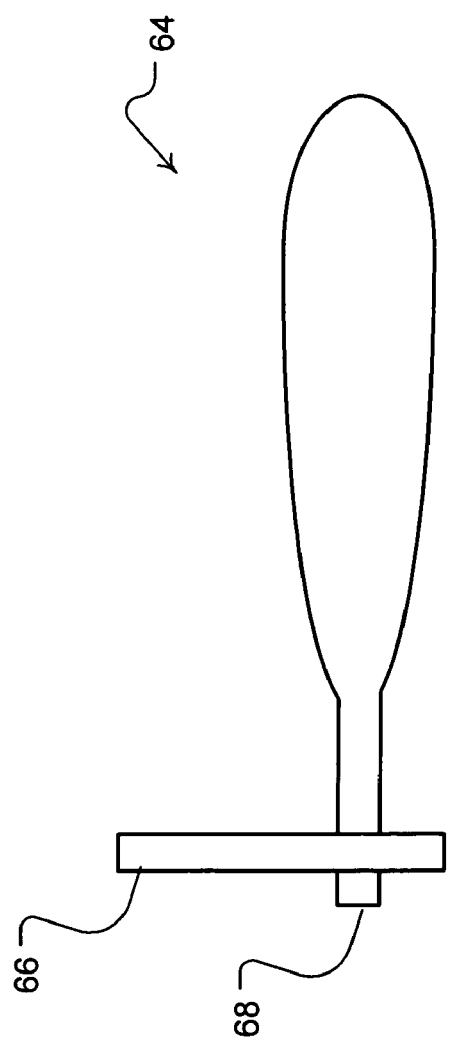
FIG. 17 is a side elevation view of the extension tool for adjusting the embodiment of the cutting block illustrated in FIG. 11.

In this embodiment, the guide extension 12 includes a cutting guide 6 of the open face variety. Optionally, a removable guide cover (e.g., a modular capture) for converting the open face guide into a slotted guide may be coupled to the guide extension 12 to convert the open face guide into a slotted guide. This is component is illustrated in FIG. 15. Optionally, the other embodiments describe herein may also be modified to receive a modular capture.

Moreover, in this embodiment an alternate engagement mechanism for selectively releasing and locking or impeding of relative movement between the main body 10 and the guide extension 12 is implemented. As illustrated in the related figures, a traversing portion 140 permits movement with regard to the guide extension 12 like the posts 14, 15 of the previous embodiments. The traversing portion 140 of the cutting block 2 is coupled with a locking pawl 52 having a toothed engagement surface 102 and a pair of holes 104. Locking pawl 52 is preferably coupled to the traversing portion 140 with pawl pin 54 through pawl pin hole 56. The pawl pin 54 is correspondingly sized with pawl pin hole 56 to permit pawl pin 54 to traverse through the pawl pin hole 56 while the pawl pin 54 is secured to the locking pawl 52. Pawl pin 54 may be fixed to locking pawl 52 in any manner after it has been located in pawl hole 56. In this regard, due to the structure of the locking pawl 52 and the width of the traversing portion 140 around which the locking pawl is coupled, the locking pawl 52 may be moved from a first locking position, extending from side PS of the traversing portion 140, traversing along the pawl pin through the pawl pin hole 56 to a second unlocked position extending from side DS of the traversing portion (see FIG. 12). Optionally, a pawl spring 58 may be coupled with the locking pawl 52 to bias the locking pawl to maintain or return to an extended position on one side which is preferably the first locking position on the proximal side. In this way, the locking pawl will have a default position which will prevent relative movement of the guide extension until movement is desired.

The guide extension of this embodiment includes a traversing portion aperture 160 which is configured to slidingly receive the traversing portion 140. The correspondingly rectangular shapes of the traversing portion 140 and the traversing portion aperture 160 permit relative axial translation between the guide extension 12 and the main body 10 but prevent rotation therebetween.

The locking pawl 52 includes teeth surface 102 that correspond with teeth 106 configured along a rack 60 in adjustment aperture 62 of the guide extension 12. When the traversing portion 140 of the main body 10 resides in the traversing portion aperture 160 of the guide extension 12, the teeth of the locking pawl 52, coupled to the traversing portion 140, engage the teeth of the rack 60 when the locking pawl 52 extends from the proximal side of the traversing portion 140 in its first locking position. Notably, the rack 60 and locking pawl 52 are positioned to engage in this way. However, when the locking pawl 52 is moved to extend from the distal side of the traversing portion 140 to its second unlocked position as previously described, the teeth of the locking pawl 52 disengage from the teeth of the rack 60. This engagement and disengagement of the teeth of the locking pawl 52 and the rack 60 respectively prevent and permits relative axial translation between the guide extension 12 and the main body 10 in the direction along the X axis.

Axial translation between the main body 10 and the guide extension 12 along axis X with this embodiment is implemented differently. In this embodiment, the traversing mechanism for generating axial extension with respect to the main body 10 and the guide extension 12 includes integrated and non-integrated components. As illustrated in 14, 16 and 17, a translation tool 64 adapted to the structure of the cutting block provides parts of the mechanism for control over the axial translation along axis X between main body 10 and the guide extension 12. The tool includes a cam 66 located about a shaft with a pivot end 68. A pivot hole 67 on the traversing portion 140 of the main body 10 of the cutting block 2 is sized to receive the pivot end 68 of the translation tool 64. When the pivot end 68 of the translation tool 64 is inserted in the pivot hole 67, the cam 66 resides in the adjustment aperture 62 of the guide extension 12. Due to the size and shape of the cam 66, during this insertion, the surface of the cam 66 facing traversing portion 140 will contact a side of the locking pawl 52 and move the locking pawl 52 from its first locked position to its second unlocked position, disengaging the teeth surface 102 of the locking pawl 52 from the teeth 106 of the rack 60.

In this position, the outer edge of the cam contacts an inner edge of the adjustment aperture 62 while the pivot end 68 resides in the pivot hole 67. Thus, absent rotation of the translation tool 64, even with the engagement pawl disengaged from the rack 60, relative movement between the main body 10 and the guide extension 12 is prevented. However, due to the off-center nature of the pivot end 68 with respect to the outer edge surface of the cam 66, rotation of the translation tool (rotational direction illustrated by arrow R in FIG. 14) will result in controlled relative axial translation between the main body 10 and the guide extension 12 as the traversing portion 140 moves within the traversing portion aperture 160. Removal of the translation tool 64 permits re-engagement of the locking pawl 52 with the rack 60, impeding additional movement between the main body 10 and the guide extension 12 until such time as the tool is utilized again. In this regard, as the translation tool 64 is withdrawn from the adjustment aperture 62, the biasing or elastic force of the pawl spring 58 returns the locking pawl from the second unlocked position to the first locked position.

Use of the three embodiments of the cutting block will now be described with respect to a resection procedure in which such a block is placed anteriorly with respect to the patient's femur. Initially, the user or practitioner places a tracker interface TI into the tracker mount 4. A tracker T may then be coupled onto the tracker interface TI. Optionally, axially translation between the main body 10 and the guide extension may be approximately centered to permit potential adjustment in either direction along the axis X if necessary during positioning. This may be performed as previously described by tactile activation of the spring loaded ball plunger 40. Preferably, based on the incision location, knee (left or right) and the side of the operation table that the camera is located an optimum orientation may be determined so that the tracker will be located outside an incision. A handle 43 may be mounted to the cutting block 2 to assist in orienting the block.

Using the tracking system, the surgeon then aligns the cutting block 2 free-hand to a desired position against the receiving surface (e.g., bone of the tibia or femur) near the location that a resection will be performed. Using the computer navigation system, the desired location may be selected within +/− a predetermined or acceptable distance or degree from the necessary resection location so as not to exceed the adjustment capabilities of the cutting block 2 which may be desirably sized for minimal invasive use. Thus, with respect to the example embodiments, initial preferred positioning may be within plus or minus 4 millimeters for purposes of proximal-distal placement along X axis. Similarly, the preferred initial positioning should be within plus or minus 3 degrees of rotation along each of the flexion/extension and varus/valgus ranges of rotation. Once so positioned, a drill with a first pin 70-1 may then be utilized to fix the cutting block 2 to the receiving surface through the centrally located swivel pin hole 18' of the swivel 20. The pin or fixing member is configured for fixable attachment to the receiving surface (e.g., the cortex of the bone).

Continuing to utilize information from the navigation system, the cutting block 2 may be moved in a direction with respect to the swivel (arrow P) to insure proper flexion/extension angle to achieve the necessary flexion/extension orientation. This movement may be controlled by practioner manipulation of a drill coupled to a second pin 70-2 when the fixing pin is inserted in a pin hole 18 of the main body 10 before the pin is fixed into the receiving surface through the pin hole 18 with the drill. For the second and third embodiments described above with wheel indents 46, when implemented, tactile positioning actuators and/or resistance actuators assist in the controlled adjustment/movement of the swivel 20 and may permit controlled incremental adjustment. Either independently or simultaneously, the cutting block 2 may be rotated with respect to the first pin 70-1 through the swivel pin hole 18' of the swivel 20 to achieve the necessary varus/valgus orientation. When the necessary position is achieved the second pin 70-2 may be fixed into the receiving surface (similar in manner to the first pin) through a pin hole 18 of the main body 10 to prevent further movement of the main body 10 of the cutting block 2. Optionally, an additional pin may be fixed through another pin hole 18 of the main body 10 to further secure the main body 10 to the receiving surface.

The next step of the procedure involves axially translating the guide extension 12 with respect to the main body 10 to adjust the resection level (at the cutting guide 6) to the necessary orientation for performing the resection. This may be performed with or without the use of the handle (which may be removed if desired). Such axial translation may be performed free-handed with the assistance of the navigation tracker only. However, as described with regard to the second and third embodiments above, controlled axial translation may be performed with the assistance of a translation mechanism. For example, the rotation of the threaded wheel type traversing mechanism 28 of the second embodiment may serve to move the cutting guide 6 into the necessary resection position in conjunction with information indicated from the navigation system. Alternatively for the third embodiment described above, a translation tool 64 with a pivoted cam may be utilized as previously described with the cutting block 2 and rotated to move the cutting guide 6 to the necessary resection position in response to information from the navigation system. After this controlled adjustment, a final pin 70-3 may be inserted as before through a pin hole 18 of the guide extension 12 to further impede any additional movement of the cutting block 2. Of course, additional pins may optionally be installed through pin holes 18 the guide extension 12 if desired. After final pin 70-3 is secured, the tracker T and tracker interface TI may be removed and the resection may be performed with a cutting instrument and the cutting guide 6.

As a result of the unique adjustment configuration as described, such a cutting block 2 may be universally used for both Tibia and Femur resections. This construction further permits use of the instrument medially, laterally or anteriorly on bone to perform proximal tibial or distal femoral resections on either left or right knees. In this regard, the adjustment capabilities and procedures for use of the blocks have previously been described with regard to an anterior placement of the block. However, as a result of the universal design, the block may also be positioned laterally or medially as well. In the case of lateral or medial placement, rotation in direction CR of the block about the first pin 70-1 through swivel pin hole 18' (i.e., about central axis C) will adjust the flexion/extension angle. For such lateral or medial placement, rotation in direction P about the pivot axis Y of the swivel will adjust the varus/valgus angle.

Finally, if the block is placed in a position which is somewhere between an anterior and medial or between an anterior and lateral placement, rotational adjustment about each axis may be compound. For example, a rotation in direction CR only about the pin through the swivel pin hole 18' may adjust both varus/valgus and flexion/extension angles. In this same position, rotation in direction P only about the pivot axis Y of the swivel may also adjust both varus/valgus and flexion/extension angles.

Moreover, since adjustment mechanisms in the cutting block provide for tactile or other controlled adjustment in the various positions, more precise positioning of the cutting block may be permitted in conjunction with information from a navigation tracker system in both varus/valgus and flexion/extension angles and distal/proximal translation.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A surgical cutting block apparatus for performing a resection procedure with a cutting instrument and for navigated orientation with a navigation tracker system, the cutting block comprising:
    a guide extension having (a) a tracker mount for use with a tracker device that provides information for a navigation system for guiding orientation of the cutting block and (b) a cutting guide for guiding a cutting instrument for a resection procedure;
    a main body coupled with the guide extension, the main body being mountable with a receiving surface to be resected; and
    a swivel coupled with the main body by a pivot, the swivel configured to receive a fixing member through the swivel, the fixing member having a first axis centrally along a length of the fixing member through the swivel, the fixing member for limiting movement of the main body with respect to the receiving surface, the pivot configured to limit relative rotation of the swivel with respect to the main body about a single axis, the single axis being generally perpendicular to the first axis.

2. The surgical cutting block apparatus of claim 1 wherein the swivel comprises a cylinder and the pivot couples to outer opposing sides of the cylinder.

3. The surgical cutting block apparatus of claim 1 wherein the swivel includes a tactile mechanism for indicating selective positioning of the swivel in its rotation about the pivot.

4. The surgical cutting block apparatus of claim 3 wherein the tactile mechanism includes metered actuators for incremental adjustment of the swivel in its rotation about the pivot.

5. The surgical cutting block apparatus of claim 3 wherein the swivel is a wheel and the tactile mechanism includes an indent coupled with a spherical body and a compression spring.

6. The surgical cutting block apparatus of claim 1 further comprising a spring biased resistance actuator for for resisting rotation of the swivel about the pivot.

7. The surgical cutting block apparatus of claim 6 wherein the spring biased resistance actuator includes a spherical ball.

8. The surgical cutting block apparatus of claim 1 further comprising a traversing mechanism coupled to the main body member and the guide extension for actuating axial extension of the guide extension with respect to the main body along a first axis generally perpendicular to a planar guide surface of the cutting guide.

9. The surgical cutting block apparatus of claim 8 wherein the traversing mechanism comprises a threaded wheel.

10. The surgical cutting block apparatus of claim 8 further comprising a tactile mechanism for indicating a relative position of extension of the guide extension with respect to the main body.

11. The surgical cutting block apparatus of claim 8 wherein the traversing mechanism comprises a rotatable cam.

12. The surgical cutting block apparatus of claim 11 wherein the rotatable cam includes a tool handle and the cam is configured for removable coupling with the main body and the guide extension.

13. The surgical cutting block apparatus of claim 12 further comprising an engagement mechanism biased for impeding relative movement between the guide extension and the main body.

14. The surgical cutting block apparatus of claim 13 wherein the engagement mechanism includes a spring.

15. The surgical cutting block apparatus of claim 14 wherein the engagement mechanism further includes a pawl and rack each having corresponding teeth configured to impede movement therebetween when in contact with each other.

16. The surgical cutting block apparatus of claim 13 wherein the cam is configured for releasing the engagement mechanism to permit relative movement between the guide extension and the main body when the cam is coupled to the cutting block to actuate axial extension of the guide extension and main body.

17. A surgical cutting block apparatus for performing a resection procedure with a cutting instrument and for navigated orientation with a navigation tracker system, the cutting block comprising:

a guide extension having (a) a tracker mount for use with a tracker device that provides information for a navigation system for guiding orientation of the cutting block and (b) a cutting guide for guiding a cutting instrument for a resection procedure;

a main body coupled with the guide extension, the main body being mountable with a receiving surface to be resected; and a swivel coupled with the main body by a pivot, the swivel configured to receive a fixing member through the swivel, the fixing member having a first axis centrally along a length of the fixing member through the swivel, the fixing member for limiting movement of the main body with respect to the receiving surface, the pivot configured to limit relative rotation of the swivel with respect to the main body about a single axis, the single axis being generally perpendicular to the first axis wherein the relative rotation of the swivel on the pivot with respect to the main body adjusts a flexion-extension angle of the cutting guide for the resection.

18. The surgical cutting block apparatus of claim 17 wherein the swivel is adapted to rotate about the fixing member through the swivel providing rotation of the swivel and main body for adjusting a varus-valgus angle of the cutting guide for the resection.

19. The surgical cutting block apparatus of claim 18 wherein the main body further includes at least one fixing member hole to accept a fixing member for fixing the main body to the receiving surface.

20. The surgical cutting block apparatus of claim 19 wherein the guide extension further includes at least one fixing member hole to accept a fixing member for fixing the guide extension to the receiving surface.

21. A surgical cutting block apparatus for performing a bone resection procedure with a cutting instrument and for navigated, orientation with a navigation tracker system, the cutting block comprising;

a guide unit fixable to a bone surface for a resection, the guide unit with a cutting guide surface for guiding a bone cutting tool for resecting the bone and a tracker mount for mounting a component of a navigation tracker system with the guide unit; and a swivel coupled to the guide unit, the swivel fixable with the bone surface with a fixing member, the swivel having a range of rotation relative to the guide unit to change the orientation of the cutting guide surface when the swivel is fixed to the bone surface with the fixing member, the swivel configured with a tactile mechanism that tactilely indicates selective positioning of the swivel in the range of rotation.

22. The surgical cutting block apparatus of claim 21 further comprising a pivot with a single pivot axis, the pivot coupled with opposing sides of the swivel, wherein the range of rotation of the swivel is limited to rotation about the single axis of the pivot.

23. The surgical cutting block apparatus of claim 22 wherein the rotation about the single axis of the pivot permits adjustment of a flexion-extension angle of the cutting guide surface for the resection.

24. The surgical cutting block apparatus of claim 23 wherein the swivel is adapted to rotate about the fixing member through the swivel providing rotation of the swivel and guide unit for adjusting a varus-valgus angle of the cutting guide surface for the resection.

25. The surgical cutting block apparatus of claim 24 wherein the guide unit includes a plurality of fixing member holes to accept a fixing member for fixing the guide unit to the receiving surface.

26. The surgical cutting block apparatus of claim 21 wherein the tactile mechanism permits incremental adjustment along the range of rotation.

27. The surgical cutting block apparatus of claim 26 wherein the swivel is a wheel and the tactile mechanism includes an indent, a spherical body and a compression spring.

28. The surgical cutting block apparatus of claim 21 further comprising a traversing mechanism, wherein the guide unit comprises a guide extension and a main body coupled to the swivel, and wherein the traversing mechanism governs actuating axial extension of the guide extension with respect to the main body along a first axis generally perpendicular to a planar guiding surface of the cutting guide surface.

29. The surgical cutting block apparatus of claim 28 wherein the traversing mechanism comprises a threaded wheel.

30. The surgical cutting block apparatus of claim 28 further comprising a tactile mechanism for indicating a relative position of extension of the guide extension with respect to the main body.

31. The surgical cutting block apparatus of claim 28 wherein the traversing mechanism comprises a rotatable cam.

32. The surgical cutting block apparatus of claim 31 wherein the rotatable cam includes a tool handle and the cam is configured for removable coupling with the main body and the guide extension.

33. The surgical cutting block apparatus of claim 32 further comprising an engagement mechanism biased for impeding relative movement between the guide extension and the main body.

34. The surgical cutting block apparatus of claim 33 wherein the engagement mechanism includes a spring.

35. The surgical cutting block apparatus of claim 34 wherein the engagement mechanism further includes a pawl and rack each having corresponding teeth configured to impede movement therebetween when in contact with each other.

36. The surgical cutting block apparatus of claim 34 wherein the cam is configured for releasing the engagement mechanism to permit relative movement between the guide extension and the main body when the cam is coupled to the cutting block to actuate axial extension of the guide extension and main body.

* * * * *